United States Patent
Chen

(10) Patent No.: US 9,974,759 B2
(45) Date of Patent: May 22, 2018

(54) BETA 2 ADRENOCEPTOR ANTAGONISTS FOR TREATING ORTHOSTATIC HYPOTENSION

(71) Applicant: Indiana University Research & Technology Corporation, Indianapolis, IN (US)

(72) Inventor: Peng-Sheng Chen, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 688 days.

(21) Appl. No.: 14/290,362

(22) Filed: May 29, 2014

(65) Prior Publication Data

US 2014/0357724 A1    Dec. 4, 2014

Related U.S. Application Data

(60) Provisional application No. 61/829,339, filed on May 31, 2013.

(51) Int. Cl.
    A61K 31/138    (2006.01)
    A61K 45/06    (2006.01)

(52) U.S. Cl.
    CPC ............ *A61K 31/138* (2013.01); *A61K 45/06* (2013.01)

(58) Field of Classification Search
    None
    See application file for complete search history.

(56) References Cited

U.S. PATENT DOCUMENTS

| | | | |
|---|---|---|---|
| 4,287,194 A | 9/1981 | Kosa et al. | |
| 6,509,317 B1 * | 1/2003 | Giroir | A61K 38/1751 514/16.4 |
| 6,830,581 B2 * | 12/2004 | Magers | A61B 18/02 607/105 |
| 7,300,932 B2 | 11/2007 | Fox et al. | |
| 7,745,665 B2 | 6/2010 | Gant et al. | |
| 7,943,628 B2 | 5/2011 | Bell et al. | |
| 8,058,304 B2 | 11/2011 | Choi et al. | |
| 8,183,293 B2 * | 5/2012 | Grillo | C07C 311/21 514/562 |
| 8,211,930 B2 | 7/2012 | Berger et al. | |
| 2002/0103117 A1 | 8/2002 | Knoell | |
| 2005/0070545 A1 | 3/2005 | Fox et al. | |
| 2006/0111416 A1 | 5/2006 | Lane et al. | |
| 2006/0194878 A1 | 8/2006 | Lopaschuk et al. | |
| 2007/0179175 A1 | 8/2007 | Lunn | |
| 2008/0227830 A1 | 9/2008 | Roberts et al. | |
| 2008/0249176 A1 | 10/2008 | Rasmussen et al. | |
| 2009/0082466 A1 | 3/2009 | Babul | |
| 2010/0080786 A1 | 4/2010 | Berger et al. | |
| 2010/0222257 A1 | 9/2010 | Gant et al. | |
| 2010/0273724 A1 | 10/2010 | Cheu et al. | |
| 2012/0121720 A1 | 5/2012 | Stamler et al. | |
| 2012/0302617 A1 | 11/2012 | Berger et al. | |
| 2013/0116286 A1 | 5/2013 | Roberts et al. | |

FOREIGN PATENT DOCUMENTS

| | | |
|---|---|---|
| EP | 1108710 A1 | 6/2001 |
| EP | 2142185 B1 | 8/2012 |
| WO | 9119513 A1 | 12/1991 |
| WO | 9526745 A1 | 10/1995 |
| WO | 0156590 A2 | 8/2001 |
| WO | 2005013907 A2 | 2/2005 |
| WO | 2005097087 A2 | 10/2005 |
| WO | 2007087452 A2 | 8/2007 |
| WO | 2008079073 A1 | 7/2008 |
| WO | 2008112773 A2 | 9/2008 |
| WO | 2008151179 A2 | 12/2008 |
| WO | 2010117423 A2 | 10/2010 |
| WO | 2012097011 A1 | 7/2012 |
| WO | 2012138214 A1 | 10/2012 |
| WO | 2012138226 A1 | 10/2012 |
| WO | 2012170578 A1 | 12/2012 |

OTHER PUBLICATIONS

Smith et al., J Pharm Technol 2013;29:23-34.*
Cleophas, et al., Angiology—The Journal of Vascular Diseases, Nov. 1986.*
Nathanson, Br. J. PHarmac. 1984, 83, 821-829.*
Shen et al., "Chronic low-level vagus nerve stimulation reduces paroxysmal atrial tachyarrhythmias in ambulatory canines by inducing structural and functional remodeling of the left stellate ganglion," Heart rhythm: the official journal of the Heart Rhythm Society. 2011:8: S502.
Onkka et al., "Sympathetic nerve fibers and ganglia in canine cervical vagus nerves: Localization and quantitation," Heart rhythm: the official journal of the Heart Rhythm Society. 2013: 10: 585-591.

* cited by examiner

*Primary Examiner* — Sreenivasan Padmanabhan
*Assistant Examiner* — Y Jeanmarie Z Calvillo
(74) *Attorney, Agent, or Firm* — Stinson Leonard Street LLP

(57) ABSTRACT

Methods of treating orthostatic hypotension are disclosed. The methods include administering to a subject in need thereof an effective amount of a beta 2 (β2) adrenoceptor antagonist, and in particular, the specific β2 adrenoceptor antagonist, 3-(isopropylamino)-1-[(7-methyl-4-indanyl)oxy]butan-2-ol.

7 Claims, 10 Drawing Sheets

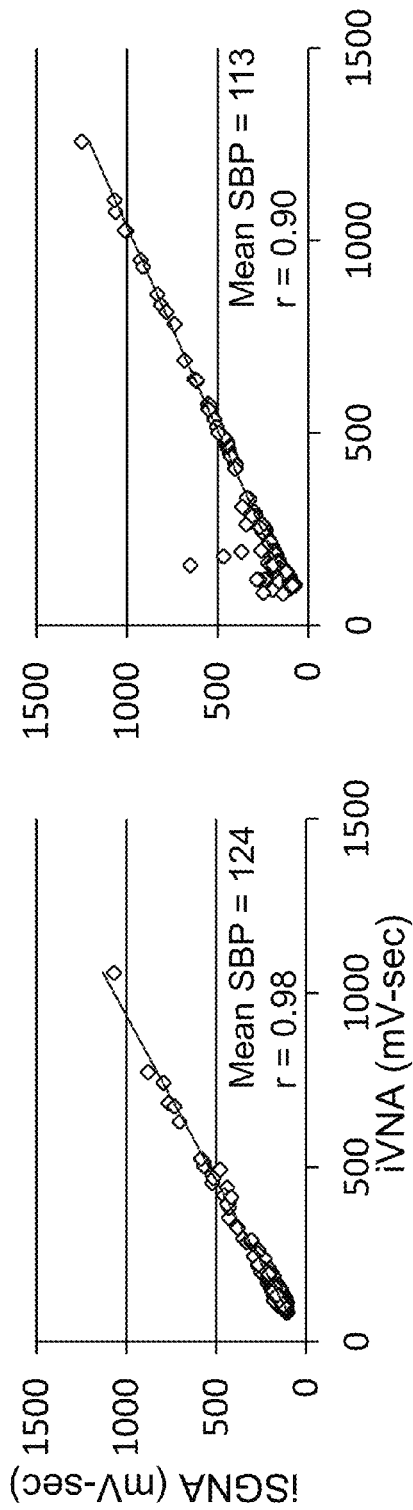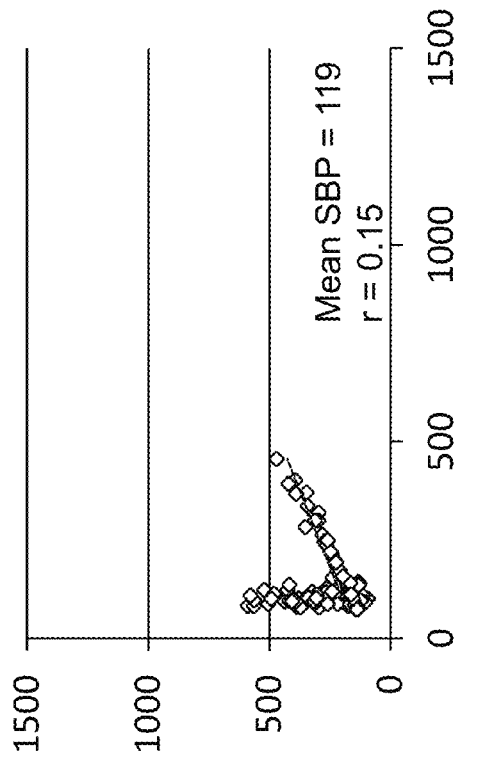
Figure 2A July
Figure 2B August
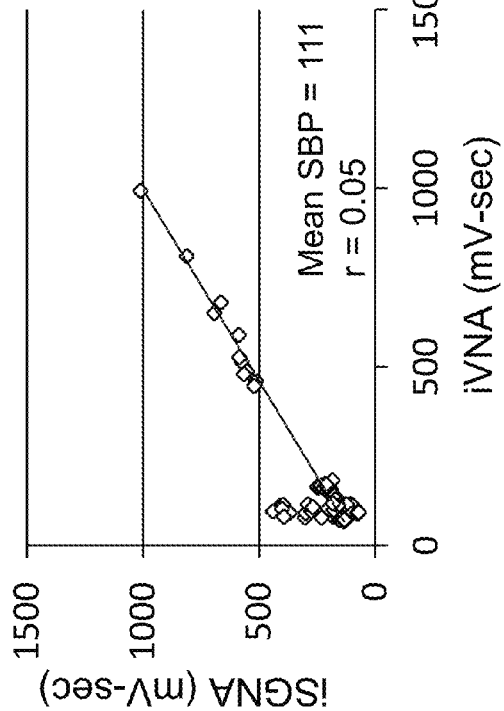
Figure 2C November
Figure 2D December

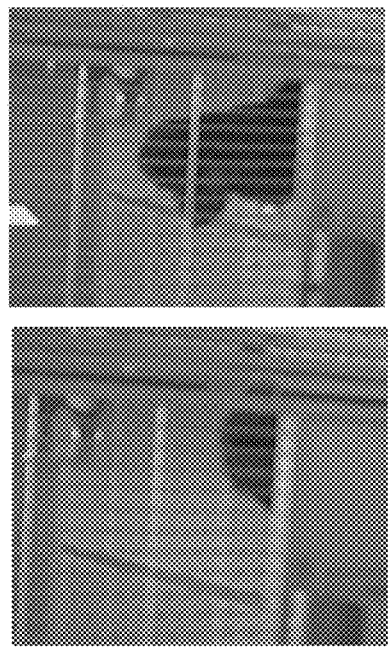
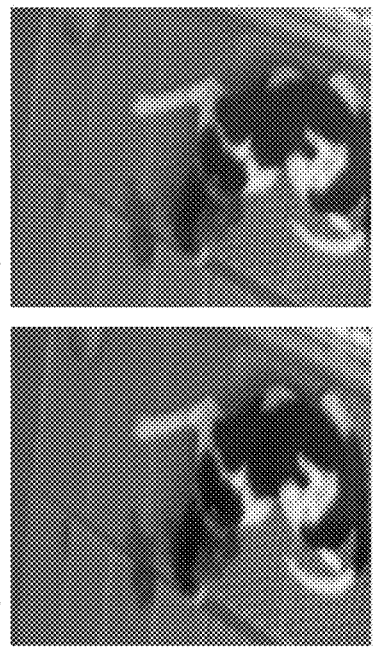
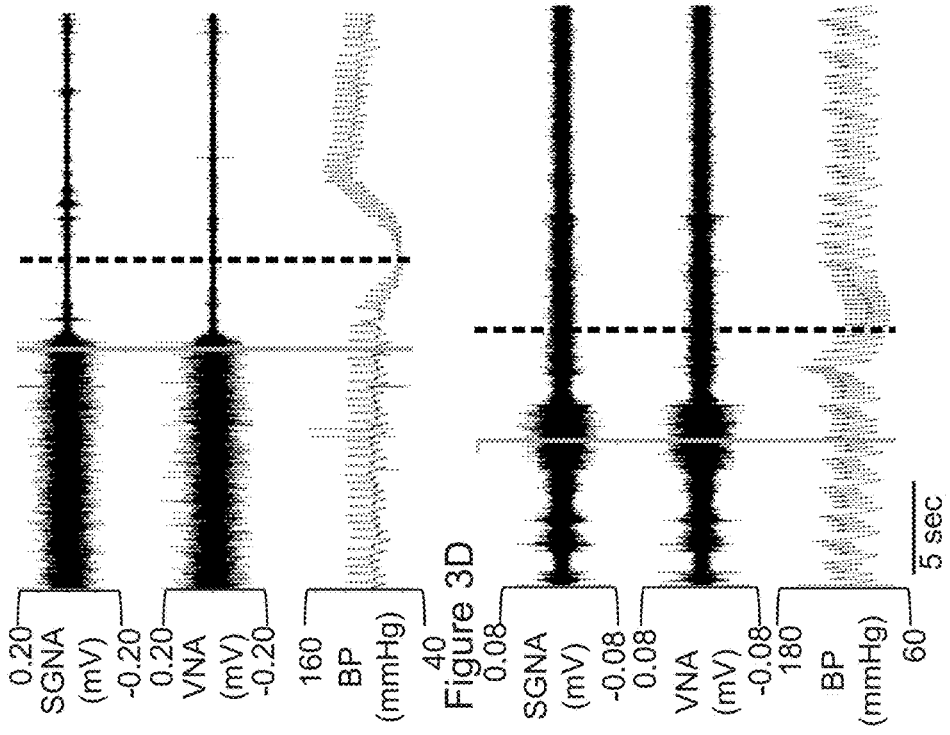
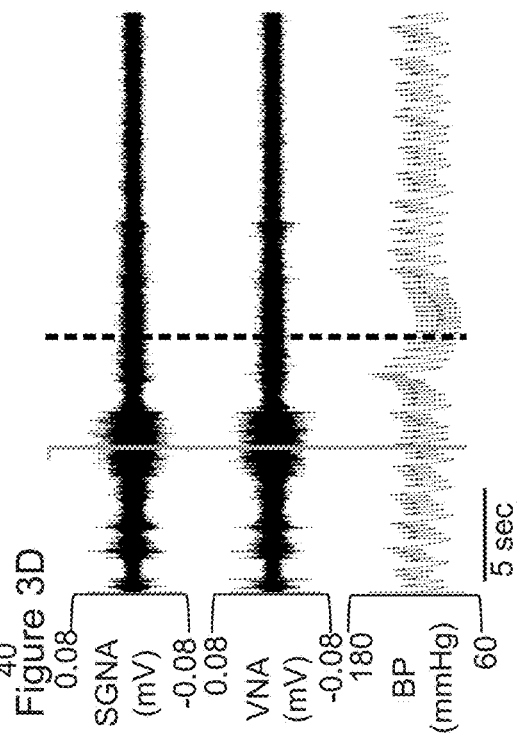
Figure 3A Figure 3B Figure 3C
Figure 3D Figure 3E Figure 3F

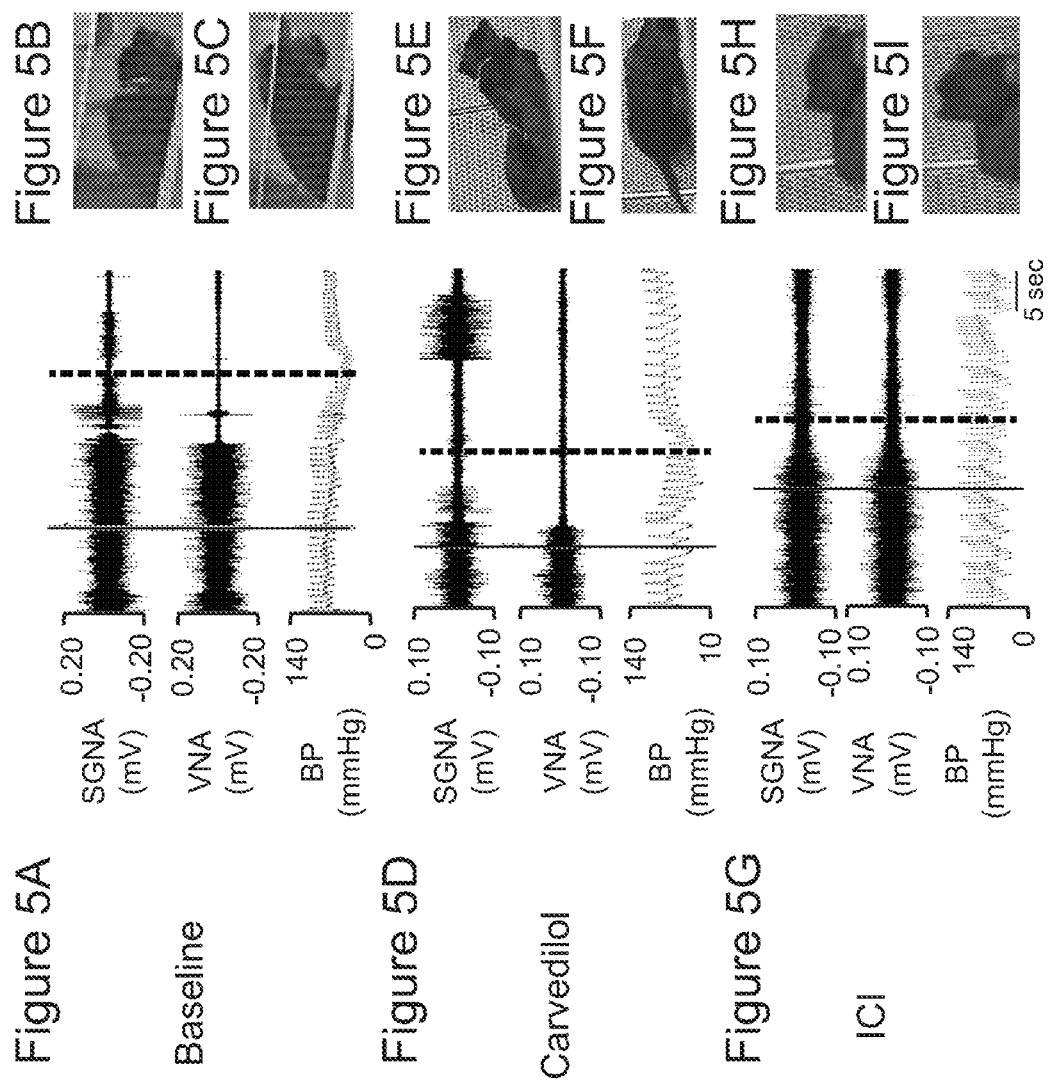

BETA 2 ADRENOCEPTOR ANTAGONISTS FOR TREATING ORTHOSTATIC HYPOTENSION

CROSS-REFERENCE TO RELATED APPLICATIONS

This application claims priority to U.S. Provisional Patent Application No. 61/829,339 filed on May 31, 2013, which is hereby incorporated by reference in its entirety.

STATEMENT OF GOVERNMENT SUPPORT

This invention was made with government support under HL071140 awarded by the National Institutes of Health. The government has certain rights in the invention.

BACKGROUND

The present disclosure relates generally to methods of treating hypotension, and in particular, orthostatic hypotension. More particularly, the present disclosure relates to methods of treating orthostatic hypotension in a subject in need thereof by administering an effective amount of a beta 2 ($\beta$2) adrenoceptor antagonist. In one embodiment, the $\beta$2 adrenoceptor antagonist is 3-(isopropylamino)-1-[(7-methyl-4-indanyl)oxy]butan-2-ol.

Low blood pressure, or hypotension, occurs when blood pressure during and after each heartbeat is lower than usual in a subject. This phenomena further results in the heart, brain, and other parts of the body not receiving sufficient blood. For some subjects, hypotension can signal an underlying problem, for example low blood volume, widening of blood vessels, anemia, heart problems, or endocrine problems, especially when it drops suddenly or is accompanied by signs and symptoms such as, for example, dizziness or light-headedness; fainting; lack of concentration; blurred vision; nausea; cold, clammy, pale skin; rapid, shallow breathing; fatigue; depression; thirst; and the like.

Orthostatic hypotension, also known as postural hypotension, however, is a common phenomenon that can occur briefly in anyone. Orthostatic hypotension occurs when a subject's blood pressure suddenly falls when changing position, such as standing up or stretching. Medically, it is defined as a fall in systolic blood pressure of at least 20 mm Hg and diastolic blood pressure of at least 10 mm Hg when a subject assumes a standing position.

While there is currently no effective drug therapy being used to treat these quick, common episodes as they typically are not considered life threatening, it would be advantageous if treatment was available, particularly for elderly subjects who are subject to falling during these episodes or younger patients who suffer from severe forms of orthostatic hypotension. Additionally, it would be beneficial if this treatment could further be administered to subjects undergoing other therapies that result in a drop in blood pressure, such as chemotherapy, as well as to subjects who suffer from dizziness or low blood pressure due to heart arrhythmias or anesthesia.

BRIEF DESCRIPTION

The present disclosure is generally related to methods for preventing, reducing, and/or treating hypotension, particularly orthostatic hypotension, or head rush. More particularly, the present disclosure relates to the use of beta 2 ($\beta$2) adrenergic receptor antagonists for preventing, reducing, and/or treating hypotension. In one particular embodiment, the $\beta$2 adrenergic receptor antagonist is 3-(isopropylamino)-1-[(7-methyl-4-indanyl)oxy]butan-2-ol, commercially available as ICI 118,551 from Akzo Nobel N.V. (Amsterdam, Netherlands).

It is well-established that the autonomic nervous system (ANS) is important in controlling not only heart rhythm and contraction, but also the vasomotor tone and systemic blood pressure (BP). Chronic stimulation of the stellate ganglion can cause hypertension in dogs, suggesting that elevated sympathetic tone is a cause of hypertension. The importance of the sympathetic nervous system in hypertension is further supported by recent studies that show renal sympathetic denervation can effectively reduce BP in subjects with drug-refractory hypertension through the reduction of sympathetic nerve activity and norepinephrine spill over. However, the relationship between sympathetic nerve activity and BP is not unidirectional because elevated BP may suppress sympathetic nerve activity through baroreflex mechanisms in humans and in ambulatory rabbits. While the activation of sympathetic perivascular nerves causes vasoconstriction, the parasympathetic or sensory arm plays an equally important role in blood pressure control through vasodilation.

In addition to its effects on peripheral vascular resistance, the autonomic nervous system also controls heart rate, which impacts diastolic filling, stroke volume, and hence the systemic BP. Additionally, in the present disclosure, it has been unexpectedly discovered that orthostatic hypotension occurs when the stellate ganglion nerve activity (SGNA) and vagal nerve activity (VNA) simultaneously terminate at the time of postural change. More particularly, preliminary data demonstrated that the stellate ganglion and vagal nerve do not fire independently of each other, but rather, there is a high degree of coordination between these two nerve structures. This pattern of correlation in part determines the spontaneous occurrences of atrial tachyarrhythmias. Among the activation patterns, simultaneous sympathovagal discharges are particularly arrhythmogenic. Given its importance to arrhythmogenesis, it is likely that the patterns of SGNA-VNA correlation also play a role in BP control in both physiologic and pathologic conditions. Accordingly, the present disclosure is directed to reducing BP fluctuation resulting from the simultaneous onset and offset of sympathovagal discharge by blocking adrenergic receptors.

Accordingly, in one aspect, the present disclosure is directed to a method for treating hypotension in a subject in need thereof. The method comprises administering a therapeutically effective amount of a $\beta$2 adrenoceptor antagonist to the subject. In one embodiment, the hypotension to be treated is orthostatic hypotension. In yet another embodiment, the hypotension to be treated is anesthesia-related hypotension.

In another aspect, the present disclosure is directed to a method for treating dizziness in a subject in need thereof. The method comprises administering a therapeutically effective amount of a $\beta$2 adrenoceptor antagonist to the subject.

In another aspect, the present disclosure is directed to a method for reducing blood pressure fluctuation in a subject in need thereof. The method comprises administering a therapeutically effective amount of a $\beta$2 adrenoceptor antagonist to the subject.

In another aspect, the present disclosure is directed to a pharmaceutical composition comprising a therapeutically effective amount of 3-(isopropylamino)-1-[(7-methyl-4-indanyl)oxy]butan-2-ol and a pharmaceutical carrier.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A depicts examples of simultaneous sympathovagal co-activation in a Group 1 dog. The asterisk indicates the start of nerve firing which occurs a few seconds prior to increase in blood pressure. FIG. 1B depicts the termination of sympathovagal firing of the same dog as analyzed in FIG. 1A after 68 seconds (not shown) of continuous firing. Note that the end of firing is followed by a sharp decrease in blood pressure. The VNA is quiescent, but intermittent small bursts of SGNA (asterisks) were present. FIG. 1C depicts nerve activity of a Group 2 dog; note the separate sympathetic and vagal firing, as marked by asterisks. SGNA was associated with increased heart rate and BP (dashed arrow). VNA was associated with reduced heart rate and BP. FIG. 1D depicts the solitary sympathetic nerve firing associated with transient increases in blood pressure. Arrows indicate bradycardia, which are associated with VNA at times when SGNA was inactive. Asterisks show intermittent SGNA, which are associated with a transient increase of BP (dashed arrows).

FIGS. 2A-2D depict the evolution of the SGNA-VNA correlation over time in dog #1, which was monitored for over 6 months. FIG. 2A shows that the dog had a linear SGNA-VNA correlation in July. Each dot represents SGNA and VNA activity integrated over 60 seconds. The patterns gradually changed to L-shaped SGNA-VNA correlation in December. Mean systolic arterial blood pressure and correlation are shown for each graph. There is no apparent relationship between the correlation patterns and the mean Systolic blood pressure (SBP).

FIGS. 3A-3F depict autonomic nerve activity and postural hypotension as analyzed in the Examples. FIGS. 3A-3C show orthostatic hypotension in dog #1. FIG. 3A shows simultaneous SGNA, VNA and BP recordings; video recordings were taken during the same time (FIGS. 3B and 3C). The solid line marks the time in the recording that corresponds to FIG. 3B and the dashed line marks the time for FIG. 3C. Note the simultaneous sympathovagal discharge while the dog is lying quietly (FIG. 3B). The termination of sympathovagal discharge occurs when the dog stands up (FIG. 3C) and resulted in a large (>20 mmHg) change in BP. FIGS. 3D-3F depict nerve activity and postural hypotension of dog #2, which shows no change in position from FIG. 3E to FIG. 3F. Note the cessation of sympathovagal discharge at the same time. However, there was only a small drop in BP (~10 mmHg) without changes in position.

FIG. 4A shows a representative hypotensive sample. Note that the hypotensive episode occurred after abrupt termination of sympathovagal discharge. FIG. 4B shows a catalogue of all hypotensive episodes in two different days, one week apart, fitted with a cubic smoothing spline (solid line). The hypotensive episodes were defined as a drop of 20 mmHg in BP over no more than 4 heart beats. The dashed lines are the point-wise 95% confidence intervals. There is strong evidence of circadian variation. P<0.001.

FIGS. 5A-5I depict responses to simultaneous termination of SGNA-VNA at baseline (FIGS. 5A-5C), during carvedilol administration (FIGS. 5D-5F) and during ICI infusion (FIGS. 5G-5I) as analyzed in the Examples. During baseline (FIG. 5A), termination of simultaneous sympathovagal discharge and change in the dog's posture from lying to sitting (FIGS. 5B-5C) resulted in a drop in BP from 110 mmHg to 80 mmHg. This same pattern is seen during carvedilol infusion (FIG. 5D), where termination of simultaneous firing and postural changes (FIGS. 5E-5F) were followed by a drop in BP from 100 mmHg to 80 mmHg. Note that during ICI infusion (FIG. 5G), there was no change in BP following termination of sympathovagal firing and postural change (FIGS. 5H-5I).

In FIG. 7A, each dot represents an averaged systolic BP over a 4-hour recording period. The dogs were color coded, showing heterogeneous BP distribution among dogs. The BP did not drop below 100 mmHg during ICI infusion (arrows). Each dot in FIG. 7B shows the average systolic BP over a 1-minute period. Data from all dogs are shown with the same color. ICI reduced the probability of BP dropping below 100 mmHg (arrows). FIG. 7C shows the relationship between integrated SGNA (iSGNA) and integrated VNA (iVNA) at baseline (upper row) and during ICI infusion (lower row). The response of nerve activities to ICI was highly heterogeneous. While in some dogs (such as dog #1 and dog #7) the nerve activity was reduced during ICI infusion as compared with baseline, in other dogs no reduction was observed.

FIG. 8A shows nerves from a Group 1 dog; note the strong TH staining (TH+%=41.5%). FIG. 8B is a section from a Group 2 dog with 16% TH staining. FIG. 8C is also from a Group 2 dog, but shows substantially less TH+staining (0.13%). These staining results emphasize the wide range of TH staining even within the same group of dogs. FIG. 8D demonstrates the presence of ganglion cells (arrows) staining positively for TH within the thoracic vagal nerve of a Group 1 dog. The objective lens used in FIGS. 8A-8D was 10× with a calibration bar of 10 μm in length.

Figure 1:
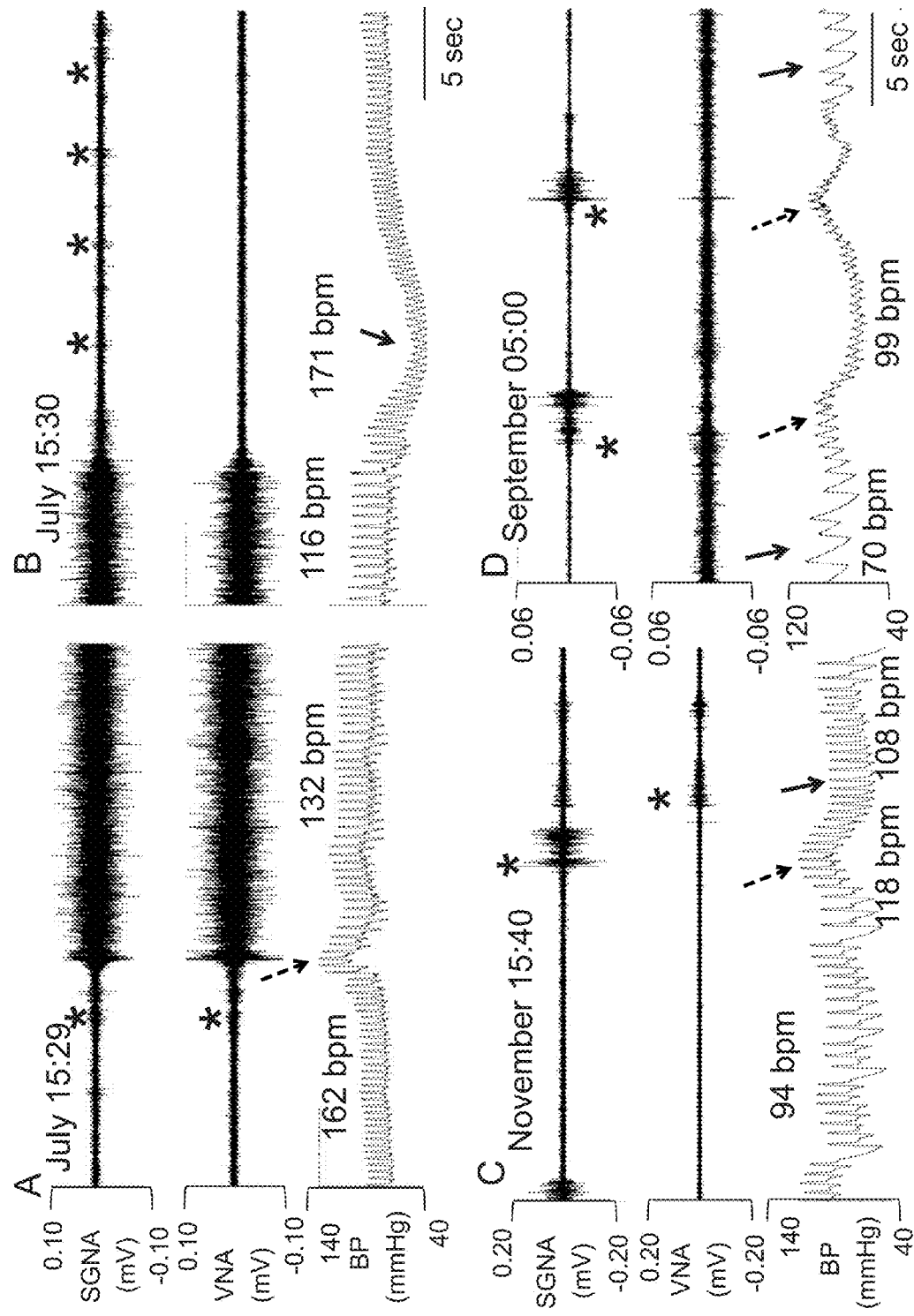
FIGS. 1A-1D depict representative autonomic nerve activity as analyzed in the Examples.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods have been discovered that prevent and protect those subjects suffering from postural orthostatic hypotension syndrome (POTS), thus preventing fainting, dizziness, and possible falling. In one aspect, the present disclosure is directed to a method for preventing POTS in a subject in need thereof. The method includes administering a therapeutically effective amount of a β2-adrenoceptor antagonist.

As used herein, "β2-adrenoceptor antagonist" refers to a high affinity antagonist that is selective for the beta adrenoceptor, and in particular to the β2 subtype adrenoceptor; that is, that specifically binds to a β2-adrenoceptor, also referred to herein as β2 adrenergic receptor.

As used herein, in the most general form, "specific binding", "binds specifically to", "specific to/for" or "specifically recognizes" refer to the ability of the antagonist to discriminate between the β2-adrenoceptor and an unrelated receptor, as determined in accordance with methods known in the art, such as, for example, selectivity profiling using cell based assays (e.g., Ricerca cell-based screen).

As used herein, "binding affinity" refers to the strength of the sum total of non-covalent interactions between a single binding site of a molecule and its binding partner. Unless indicated otherwise, as used herein, "binding affinity" refers to intrinsic binding affinity which reflects a 1:1 interaction between members of a binding pair (e.g., an antagonist and receptor). The dissociation constant "KD" is commonly used to describe the affinity between a molecule (such as an antagonist) and its binding partner (such as a receptor), i.e., how tightly a ligand binds to a particular protein. Ligand-protein affinities are influenced by non-covalent intermolecular interactions between the two molecules. Affinity can be measured by common methods known in the art, including, for example, surface plasmon resonance or isothermal titration calorimetry.

As used herein, "hypotension" refers to a condition that occurs when blood pressure during and after each heartbeat is lower than usual in a subject. More specifically, hypotension refers to a fall in systolic blood pressure of at least 20 mm Hg and diastolic blood pressure of at least 10 mm Hg. Hypotension can be the result of, for example, dehydration, severe bleeding, organ inflammation, heart disease (e.g., myocarditis, aortic stenosis, pericarditis, pulmonary embolism, bradycardia), medication-induced hypotension (e.g., anesthesia, chemotherapy), vasovagal reaction, orthostatic hypotension, micturition syncope, adrenal insufficiency (e.g., Addison's Disease), septicemia, anaphylaxis, and the like. In particular embodiments, the subject suffers from episodes of orthostatic hypotension.

As used herein, "severe bleeding" refers to a condition in which a subject loses greater than 15% of total blood volume, including greater than 20% of total blood volume, including greater than 30% of total blood volume, and including greater than 40% of total blood volume.

As used herein, "elderly subject", refers to a subject of at least 45 years of age, including at least 50 years of age, including at least 55 years of age, including at least 60 years of age, including at least 65 years of age, including at least 70 years of age, including at least 75 years of age, including at least 80 years of age, further including from about 55 years of age to about 80 years of age.

As used herein, "susceptible" and "at risk" refer to having little resistance to a certain disease, disorder or condition, and in particular, to hypotension, including being genetically predisposed, having a family history of, and/or having symptoms of the disease, disorder or condition.

All combinations of method or process steps as used herein can be performed in any order, unless otherwise specified or clearly implied to the contrary by the context in which the referenced combination is made.

DETAILED DESCRIPTION

In accordance with the present disclosure, methods have been discovered that surprisingly allow for the prevention, reduction, minimization, and/or treatment of hypotension, and hypotension episodes. Particularly, antagonists that specifically bind to the β2-adrenoceptor are administered, inhibiting adrenergic receptor activation. This inhibition reduces blood pressure fluctuation such as caused by the simultaneous onset and offset of sympathovagal discharge. The methods provide for protection from hypotension episodes that can lead to fainting, dizziness, and possible falling to subjects in need thereof.

Methods of Administering β2-Adrenoceptor Antagonists

The methods of the present disclosure generally include the administration of one or more beta-adrenoceptor antagonists, and in particular, β2-adrenoceptor antagonists, to a subject in need thereof to prevent/minimize/control blood pressure fluctuations, and in particular, hypotension episodes due to sudden blood pressure drop. Particularly, the methods of the present disclosure can prevent/minimize/reduce/control/treat hypotension, such as orthostatic hypotension, in subjects in need thereof; that is, by preventing/minimizing/controlling blood pressure fluctuations, the methods can prevent/reduce/control/treat hypotension episodes, thereby preventing/controlling/reducing/treating symptoms of the episodes including fainting, dizziness, lightheadedness, and possible falling.

Beta-adrenoceptors are coupled to the stimulatory G protein. The alpha subunit of the G protein activates adenylyl cyclase, which catalyzes the production of cyclic adenosine monophosphate (cAMP). In the lung, cAMP causes a decrease in the intracellular calcium concentration and, via activation of protein kinase A, both inactivates myosin light chain kinase and activates myosin light chain phosphatase. In addition, β2 adrenoceptors open large conductance calcium-activated potassium channels and thereby tend to hyperpolarize airway smooth muscle cells. The combination of decreased intracellular calcium, increased membrane potassium conductance, and decreased myosin light chain kinase activity leads to smooth muscle relaxation and bronchodilation. Accordingly, by binding to β2 adrenoceptors, the methods of the present disclosure can prevent/minimize/control blood pressure fluctuations, further preventing/reducing/controlling/treating hypotension episodes as compared to subjects that are not administered the β2 adrenoceptor antagonist.

The β2 adrenoceptor antagonist described below in detail and used in the methods of the present disclosure can be administered to a subset of subjects in need of preventing/minimizing/controlling blood pressure fluctuations. Some subjects that are in specific need of restored/maintained blood pressure levels may include subjects who are susceptible to, or at elevated risk of, experiencing hypotension episodes, including subjects susceptible to, or at elevated risk of, dehydration, severe bleeding, organ inflammation, heart disease (e.g., myocarditis, aortic stenosis, pericarditis, pulmonary embolism, bradycardia), anesthesia, chemotherapy, vasovagal reaction, orthostatic hypotension, micturition syncope, adrenal insufficiency, septicemia, anaphylaxis, and the like. Particularly, the method can be administered to elderly subjects who may be more likely to fall due to a hypotension episode. In one particular embodiment, the methods can be administered to a subject who has, or is susceptible to, or at elevated risk of, orthostatic hypotension. Subjects may be susceptible to, or at elevated risk of, experiencing hypotension episodes/situations due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

The β2 adrenoceptor antagonist can be administered alone in a suitable pharmaceutical formulation (i.e., no other active compound) or as a component of a suitable pharmaceutical formulation comprising the antagonist in combination with another active compound. Additionally, the β2 adrenoceptor antagonist, alone or in combination with another active compound, may be used in the manufacture of one or more medicaments. The pharmaceutical formulations may include one or more pharmaceutically acceptable carriers as are known in the art. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the formulation and not injurious to the subject. Lyophilized formulations, which may be reconstituted and administered, are also within the scope of the present disclosure.

Pharmaceutically acceptable carriers may be, for example, excipients, vehicles, diluents, and combinations thereof. For example, where the formulations are to be administered orally, they may be formulated as tablets, capsules, granules, powders, or syrups; or for parenteral administration, they may be formulated as injections (intramuscular, subcutaneous, intramedullary, intrathecal, intraventricular, intraperitoneal, intravenous), drop infusion preparations, or suppositories. These formulations can be prepared by conventional means, and, if desired, the active compound (i.e., β2 adrenoceptor antagonists) may be mixed with any conventional additive, such as an excipient, a binder, a disintegrating agent, a lubricant, a corrigent, a solubilizing agent, a suspension aid, an emulsifying agent, or a coating agent.

β2 Adrenoceptor Antagonists

One particularly suitable β2 adrenoceptor antagonist is 3-(isopropylamino)-1-[(7-methyl-4-indanyl)oxy]butan-2-ol (available as ICI-118,551 from Akzo Nobel N.V. (Amsterdam, Netherlands). ICI-118,551 is a selective β2 adrenoceptor antagonist, binding to the β2 subtype with at least 100 times greater affinity than β1 or β3, the two other known subtypes of the beta adrenoceptor. Other suitable β2 adrenoceptor antagonists include, for example, salbutamol, levosalbutamol, terbutaline, pirbuterol, procaterol, clenbuterol, metaproterenol, fenoterol, bitolterol mesylate, ritodrine, isoprenaline, salmeterol, formoterol, bambuterol, clenbuterol, indacaterol, and combinations thereof (chemical structures shown in Table 1 below).

TABLE 1

| Common Name | IUPAC Name | Chemical Structure |
|---|---|---|
| Salbutamol | (RS)-4-[2-(tert-butylamino)-1-hydroxyethyl]-2-(hydroxymethyl)phenol | 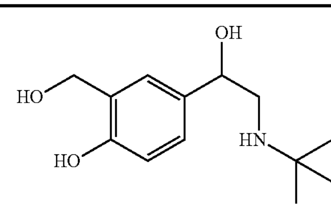 |
| Terbutaline | (RS)-5-[2-(tert-butylamino)-1-hydroxyethyl]benzene-1,3-diol | 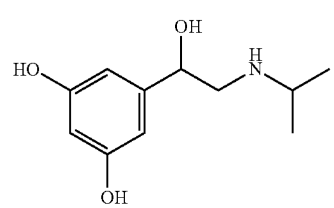 |
| Isoprenaline | (RS)-4-[1-hydroxy-2-(isopropylamino)ethyl]benzene-1,2-diol | 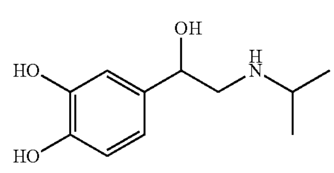 |

TABLE 1-continued

| Common Name | IUPAC Name | Chemical Structure |
|---|---|---|
| Levosalbutamol | 4-[(1R)-2-(tert-butylamino)-1-hydroxyethyl]-2-(hydroxymethyl)phenol | 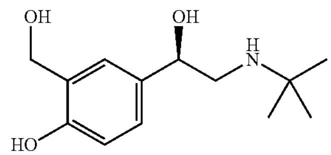 [SMILES: CC(C)(C)NC[C@H](O)c1ccc(O)c(CO)c1] |
| Metaproterenol | (RS)-5-[1-hydroxy-2-(isopropylamino)ethyl]benzene-1,3-diol | 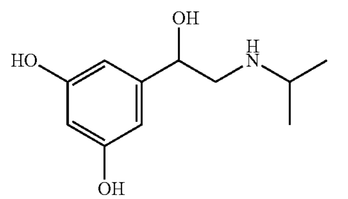 |
| Pirbuterol | (RS)-6-[2-(tert-butylamino)-1-hydroxyethyl]-2-(hydroxymethyl)pyridin-3-ol | 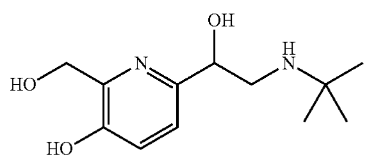 [SMILES: CC(C)(C)NCC(O)c1ccc(O)c(CO)n1] |
| Procaterol | (±)-(1R,2S)-rel-8-Hydroxy-5-[1-hydroxy-2-(isopropylamino)butyl]-quinolin-2(1H)-one | 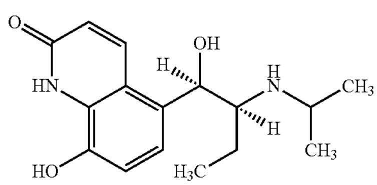 [SMILES: CC[C@H](NC(C)C)[C@H](O)c1ccc(O)c2[nH]c(=O)ccc12] |
| Clenbuterol | (RS)-1-(4-Amino-3,5-dichlorophenyl)-2-(tert-butylamino)ethanol | 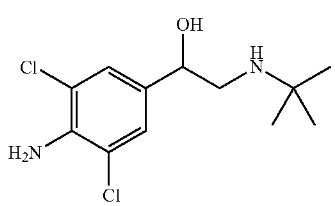 [SMILES: CC(C)(C)NCC(O)c1cc(Cl)c(N)c(Cl)c1] |
| Fenoterol | (RR,SS)-5-(1-hydroxy-2-{[2-(4-hydroxyphenyl)-1-methylethyl]amino}ethyl)benzene-1,3-diol | 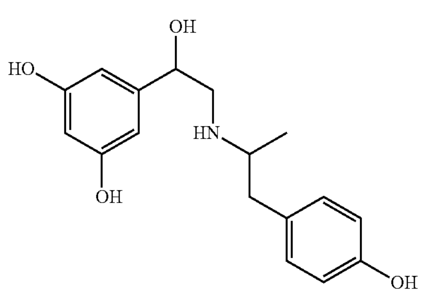 [SMILES: CC(Cc1ccc(O)cc1)NCC(O)c1cc(O)cc(O)c1] |

TABLE 1-continued

| Common Name | IUPAC Name | Chemical Structure |
|---|---|---|
| Bitolterol mesylate | (RS)-[4-(1-Hydroxy-2-tert-butylamino-ethyl)-2-(4-methylbenzoyl)oxy-phenyl] 4-methylbenzoate | 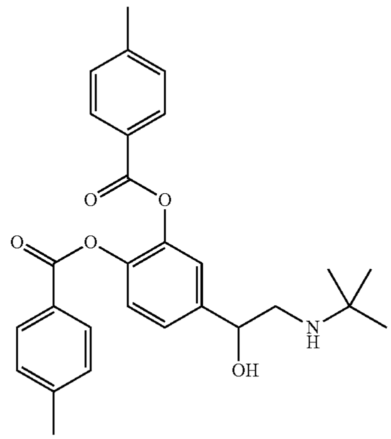 [SMILES: Cc1ccc(C(=O)Oc2ccc(C(O)CNC(C)(C)C)cc2OC(=O)c2ccc(C)cc2)cc1] |
| Ritodrine | 4-(2-((1R,2S)-1-hydroxy-1-(4-hydroxyphenyl)propan-2-ylamino)ethyl)phenol | 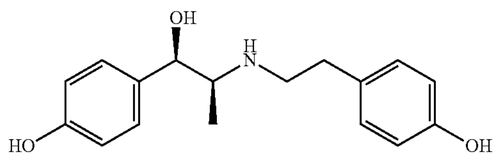 [SMILES: C[C@H](NCCc1ccc(O)cc1)[C@H](O)c1ccc(O)cc1] |
| Salmeterol | (RS)-2-(hydroxymethyl)-4-{1-hydroxy-2-[6-(4-phenylbutoxy)hexylamino]ethyl}phenol | 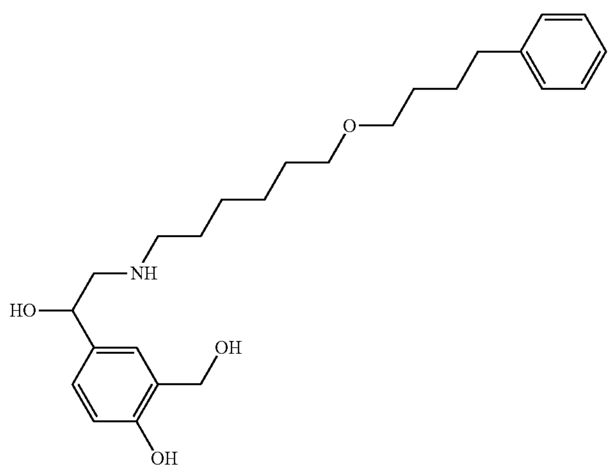 [SMILES: OCc1cc(C(O)CNCCCCCCOCCCCc2ccccc2)ccc1O] |
| Formoterol | rac-(R,R)-N-[2-hydroxy-5-[1-hydroxy-2-[1-(4-methoxyphenyl)propan-2-ylamino]ethyl]phenyl]formamide | 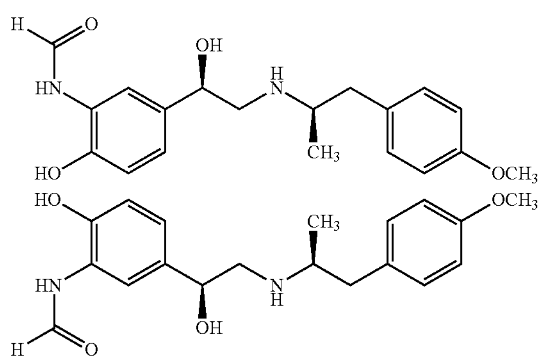 |

TABLE 1-continued

| Common Name | IUPAC Name | Chemical Structure |
|---|---|---|
| Bambuterol | (RS)-5-[2-(tert-butylamino)-1-hydroxyethyl]benzene-1,3-diyl bis(dimethylcarbamate) | 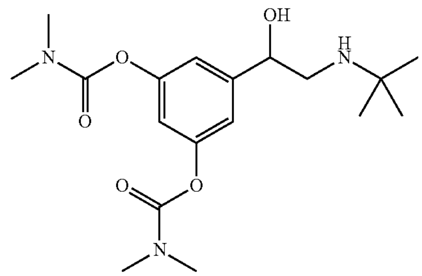 [SMILES: CN(C)C(=O)Oc1cc(OC(=O)N(C)C)cc(C(O)CNC(C)(C)C)c1] |
| Indacaterol | (R)-5-[2-[(5,6-Diethyl-2,3-dihydro-1H-inden-2-yl)amino]-1-hydroxyethyl]-8-hydroxyquinolin-2(1H)-one | 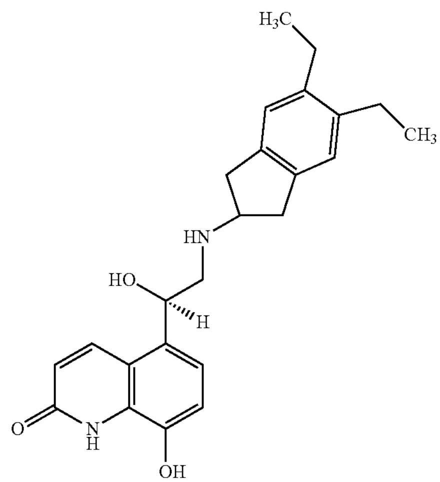 [SMILES: CCc1cc2c(cc1CC)CC(NC[C@H](O)c1ccc(O)c3[nH]c(=O)ccc13)C2] |

Actual dosage levels of the β2 adrenoceptor antagonist in a pharmaceutical formulation for use in the methods of the present disclosure may be varied so as to obtain an amount of the β2 adrenoceptor antagonist that is effective to achieve the desired therapeutic response or benefit for a particular subject, formulation, and/or mode of administration. More particularly, as used herein, the phrase "therapeutically effective amount" of the β2 adrenoceptor antagonist used in the methods of the present disclosure refers to a sufficient amount of a β2 adrenoceptor antagonist to treat hypotension as defined herein, at a reasonable benefit/risk ratio applicable to any medical treatment. It can be understood, however, that the total daily usage of the β2 adrenoceptor antagonist and pharmaceutical formulations including the β2 adrenoceptor antagonists for use in the methods of the present disclosure can be decided by the attending physician within the scope of sound medical judgment. The specific therapeutically effective dose level for any particular subject can depend upon a variety of factors including the hypotension episode being treated and the severity of the episode; activity of the specific β2 adrenoceptor antagonist employed; the specific pharmaceutical formulation employed; the age, body weight, general health, sex and diet of the subject; the time of administration, route of administration, and rate of excretion of the specific β2 adrenoceptor antagonist employed; the duration of the treatment; drugs used in combination or coincidental with the specific β2 adrenoceptor antagonist employed; and like factors well-known in the medical arts. For example, it is well within the skill of the art to start doses of the β2 adrenoceptor antagonist at levels lower than required to achieve the desired therapeutic effect and to gradually increase the dosage until the desired effect is achieved.

In some embodiments, the β2 adrenoceptor antagonist can be administered to a subject in need thereof in an amount ranging from about 1 µg/kg total body weight of the subject to about 5 µg/kg total body weight of the subject per hour for a period of about 7 days. In one embodiment, the methods of the present disclosure include administering to a subject in need thereof an amount of about 3.1 µg/kg total body weight of the subject per hour for a period of about 7 days. In some embodiments, the β2 adrenoceptor antagonist can be administered to a subject in need thereof in amounts of from about 5 µg to about 30 µg, including about 10 µg, per hour for a period of about 7 days. In particular embodiments, the β2 adrenoceptor antagonist can be administered orally to a subject in need thereof in amounts of from about 10 mg to about 40 mg, and including from about 15 mg to about 35 mg, at regular intervals including every 2 hours, including every 4 hours, including every 8 hours, including every 12 hours, including every 24 hours, and including every 48 hours. If administered as a daily dosage of β2 adrenoceptor antagonists or pharmaceutical formulation including the β2 adrenoceptor antagonists, the β2 adrenoceptor antagonists or pharmaceutical formulation including the β2 adrenoceptor antagonists may be in the form of a single dosage or may be in the form of two dosages, three dosages, four dosages or more to be administered two or more times during the day.

It should be understood that the pharmaceutical compositions of the present disclosure can further include additional known therapeutic agents, drugs, modifications of the β2 adrenoceptor antagonists into prodrugs, and the like for alleviating, mediating, preventing, and treating hypotension.

The disclosure will be more fully understood upon consideration of the following non-limiting Examples.

EXAMPLES

Protocol 1: Ambulatory Monitoring of Autonomic Nerve Activities and BP

Eight mongrel dogs (4 male, weighing 20-30 kg) were used in this Example. Left thoracotomy was performed through the first intercostal space for the implantation of a D70-CCTP radiotransmitter manufactured by the Data Sciences International (DSI, St Paul, Minn.). The first pair of bipolar electrodes was inserted beneath the nerve sheath of the left stellate ganglion. A second pair of bipolar leads was attached to the left thoracic vagal nerve at a level of 4 to 5 cm above the aortic arch. The third lead, a catheter with a pressure sensor, was inserted directly into the subclavian artery for blood pressure (BP) recording. The transmitter and ground wires were inserted into a subcutaneous pocket. The chest wall was then closed.

After 2 weeks of recovery, the radiotransmitter was turned on to record nerve signals and BP at baseline. The pre-implantation BP was calibrated against the ambient pressure in the vivarium. There was a 12-hour daylight cycle in the vivarium staring at 7 AM each day. After the baseline (stellate ganglion nerve activity (SGNA), vagal nerve activity (VNA), and BP) recordings, the dogs were given oral carvedilol, 12 mg twice daily for a week. The drugs were then washed out for a week and baseline recordings were re-collected. The dogs were brought back to the sterile surgical suite for minor surgery that included subcutaneous implantation of a 2-ml osmotic pump (model 2ML1) manufactured by Alzet Inc. (Cupertino, Calif.). The pump contained 2 ml of $ddH_2O$ and 18 mg of ICI-118,551 (ICI). The pump is designed to empty its contents over 7 days at a rate of 10 µl/hr. Therefore, the infusion rate was 3.1 µg/kg/hr for a 30 kg dog. The infusion rate at which half the $\beta_2$-receptors are saturated has been reported to be 2 µg/kg in beagles. The data collected at days 6-7 of the infusion were used for analyses. A week after completing this stage of drug infusion, the dogs were euthanized. The left stellate ganglion and the left thoracic vagal nerves were then harvested for histological and immunohistochemical analyses.

Protocol 2: Sympathetic Component in the Thoracic Vagal Nerve and Simultaneous Sympathovagal Discharges Because the results of Protocol 1 showed significant blood pressure fluctuations associated with simultaneous sympathovagal discharges, it was hypothesized that the amount of sympathetic nerve fibers within the thoracic vagal nerve in part determined whether the dogs had simultaneous sympathovagal discharges and were prone to BP fluctuations. Therefore, dogs were chosen from previous studies that had both histological materials and nerve recordings available for the instant analysis. In addition to dogs from Protocol 1, 12 additional dogs that underwent baseline recordings of the SGNA and VNA using a DSI D70-EEE radiotransmitter were included. After 2-3 weeks of recovery after the surgical implantation of the DSI transmitters, baseline nerve activities were recorded while the dogs were ambulatory. At the end of the experiments, the left thoracic vagal nerves of those dogs were harvested for immunohistochemical studies.

Data Analyses

Nerve Activity Analyses

Nerve activities were analyzed both manually and with assistance of computerized methods as set forth in Shen et al., "Chronic low-level vagus nerve stimulation reduces paroxysmal atrial tachyarrhythmias in ambulatory canines by inducing structural and functional remodeling of the left stellate ganglion," Heart rhythm: the official journal of the Heart Rhythm Society. 2011:8: S502, incorporated herein by reference to the extent it is consistent herewith. The nerve activities were integrated minute-by-minute. Because BP recordings are prone to motion artifacts, the data of all dogs included in Protocol 1 was manually reviewed and the first 10 noise-free minutes of each hour were selected for analyses. The mean BP was also analyzed minute-by-minute during the same period. The SGNA was plotted against the VNA on an XY graph to visualize the patterns of activation. Pearson correlation coefficients between these two nerve activities were calculated. The data obtained from the manual analyses were subjected to further statistical analyses as described below.

Immunocytochemical Staining

The left thoracic vagal nerves (N=20) were fixed with 4% formalin for 45-60 minutes before transfer to 70% ethyl alcohol. The nerves were embedded in paraffin and 5 µm thick cross sections were cut and stained with tyrosine hydroxylase for sympathetic (adrenergic) nerves. The programs Adobe Photoshop CS5.1 and Magic Wand were used to localize the TH positive portions and calculate their cross sectional areas respectively according to the method described in Onkka et al., "Sympathetic nerve fibers and ganglia in canine cervical vagus nerves: Localization and quantitation," Heart rhythm: the official journal of the Heart Rhythm Society. 2013:10:585-591, incorporated herein by reference to the extent it is consistent herewith. The cross-sectional area of each vagus nerve was then compared with the SGNA-VNA correlation coefficient at baseline.

Statistical Analyses

Data were summarized as mean±standard deviation and ranges for continuous variables and percentages for binary variables were determined Parameter estimates were expressed as point estimates and 95% confidence intervals (CI). To determine the relationship between BP, heart rate (HR) and ANS activities, 1-minute and 4-hour averages for each dog were calculated on each day of data collection starting at midnight. Pearson correlation coefficients between SGNA and VNA were also calculated within each 4-hour interval. To analyze data from any given individual dog, multiple linear regression with systolic BP as the dependent variable and ANS activities as the independent variables based on 1-minute average data were used. To analyze data from all dogs and the 4-hour average data, a random effects model with dog as the random effect was used with the same dependent and independent variables, plus HR and the Pearson correlation coefficient as additional independent variables. Random effects models were also used to compare the effects of the drugs against baseline on BP, each of the ANS activities, and the proportion of hypotensive episodes (average systolic arterial pressure (SAP)<100 mmHg) using data from all dogs, which included the main effects of drug and the six 4-hour intervals and their interactions. A cubic smoothing spline was also used to fit BP versus hour for one dog. Statistical analysis was performed with IBM SPSS Statistics 19 (Armonk, N.Y.) and SAS version 9.3 (SAS Institute Inc., Cary, N.C.). A two-sided p value of ≤0.05 was considered statistically significant.

Results

Protocol 1: Ambulatory Monitoring of Autonomic Nerve Activities and BP

Relationship Between Autonomic Nerve Activity and BP

Each dog was monitored for an average of 10 weeks (range 6 to 21 weeks) during which SGNA, VNA and BP were intermittently collected. As previously reported, there are two basic patterns of nerve activity. In the first pattern (termed "Group 1" in that report), the SGNA and VNA activate simultaneously (FIGS. 1A and 1B). A plot of integrated stellate ganglion nerve activity (iSGNA) versus integrated vagal nerve activity (iVNA) gives a linear pattern (FIG. 2A). Five of the eight dogs demonstrated Group 1 firing upon baseline recording. The SGNA-VNA correlation is important in BP control. In general, simultaneous sympathovagal firing (which only occurred in Group 1 dogs) was associated with a higher mean BP, but incongruously, more extreme drops in BP at the time of simultaneous sympathovagal termination. BP is a product of heart rate, stroke volume and total peripheral vascular resistance. Because the stroke volume depends in part on diastolic filling, an abrupt increase or decrease in heart rate may decrease or increase stroke volume, respectively. The beat-to-beat variation in blood pressure and nerve activity is therefore complex, as illustrated by FIGS. 1A-1D.

FIG. 1A shows a Group 1 dog with a baseline BP ranging from 75 to 100 mmHg and heart rate averaging 162 bpm. At the start of the simultaneous low amplitude sympathovagal discharge (asterisk), the BP started to increase rapidly. Abrupt increase in BP (dashed arrow) was associated with sustained and large amplitude simultaneous sympathovagal discharges without apparent initial increase in HR, probably due to a large parasympathetic tone provided by vagal nerve. (The BP dropped after the dashed arrow with associated slowing of the heart rate to 132 bpm, which could be a response to increased vagal activity.) FIG. 1B shows that after 68 seconds of continuous sympathovagal discharge, the nerve activity abruptly and simultaneously terminated, which was followed by a rapid drop in BP to as low as 65 mmHg systolic and 45 mmHg diastolic (black arrow) and tachycardia. The BP then gradually recovered, assisted by low amplitude intermittent SGNA (asterisks). The abrupt termination of sympathovagal discharge and subsequent drop in BP, followed by gradual recovery, was observed in all Group 1 dogs. The termination of vagal nerve discharge resulted in an abrupt increase in heart rate that transiently reduced stroke volume by decreasing diastolic ventricular filling. In addition, a simultaneous loss of sympathetic support of the peripheral vascular resistance contributed to the abrupt BP reduction. The persistent increase in heart rate and intermittent SGNA activity (asterisks in FIG. 1B) led to gradual increase in BP after the hypotensive episode. An additional factor in the abrupt BP reduction may be due to coincidental change of posture, as presented below.

The second pattern of nerve activity (Group 2), where SGNA and VNA activate separately, is shown in FIG. 1C. Note that the independent activation of SGNA (asterisk, first line) was associated with elevated BP (dashed arrow) while VNA (asterisk, second line) was associated with a lower mean arterial BP and HR. This represents the classic baroreflex response with VNA excitation and reduction of SGNA resulting in a rapid normalization of BP. FIG. 1D shows a second dog in which SGNA and VNA activated separately— here the vagus nerve activates alone during the first eight seconds of the recording. This activation was associated with bradycardia (black arrow). The sympathetic bursts were low amplitude (asterisks) in the beginning and were associated with brief increases in HR (dashed arrows) and BP. This was followed by a large increase of SGNA and a simultaneous drop of BP. Complete cessation of SGNA and continuous VNA was associated with bradycardia (second black arrow). In this case, bradycardia resulted in SGNA excitation with episodic increase in the BP and heart rate. However, the persistent VNA excitation (particularly without low-amplitude SGNA excitation) eventually lead to bradycardia.

Changing Sympathovagal Correlation

A previous study that monitored canines for approximately 2 months, suggested that the sympathovagal correlation is static. However, recordings done in the present Examples over a longer time frame (5-6 months) demonstrated that patterns of sympathovagal correlation evolve over time. This is best illustrated by dog #1 that was monitored over 6 months, as shown in FIGS. 2A-2D. This dog started out during the monitoring period (July) as a Group 1 dog (FIG. 2A). At that time, the dog was 6 months old and weighed 30.1 kg. Slowly, over months, he evolved into a Group 2 dog (FIGS. 2B-2D). The dog's weight increased to 40.3 kg in December. iSGNA and iVNA dropped drastically in December. There were increasing SGNA at the time when VNA was silent. This nonlinear relationship between SGNA and VNA indicates a complex interaction between SGNA and VNA. Other dogs stayed in the same group throughout the recording, although the patterns of correlation changed slightly over time. Particularly, a linear regression model showed that the VNA was negatively associated with BP ($p=0.0297$), while SGNA was positively (but insignificantly) associated with BP ($p=0.0544$) in July, when there was linear sympathovagal correlation. The SGNA was positively correlated with BP ($p=0.0213$) in August, but the VNA no longer had significant effects on BP ($p=0.4776$). No significant relationship between SGNA and BP or between VNA and BP was found during November in this dog (Group 2 state). For all dogs studied, each mV-s increase of iSGNA was associated with a 0.04580 mmHg increase in BP ($p=0.0478$). Each mV-s increase of iVNA was associated with an insignificant decrease in BP of $-0.05484$ mmHg ($p=0.0648$). Heart rate ($p=0.9991$) and the SGNA-VNA correlation coefficient ($p=0.1294$) were not associated with BP changes using analyses summarized by 4-hour intervals. However, as reported in the previous section, instantaneous changes in BP may occur on a shorter time scale and therefore were not reflected in the BP or ANS average over one minute.

Abrupt Hypotensive Episodes

As shown in FIG. 1B, abrupt cessation of simultaneous sympathovagal discharges seen in Group 1 dogs was associated with an abrupt drop in BP. To determine if these episodes were related to postural changes, video cameras were installed in the dog kennel and monitored nerve activity, BP and video simultaneously. Several patterns of behavior emerged as is shown in FIGS. 3A-3F. The first pattern is illustrated in FIGS. 3A-C. FIG. 3A shows simultaneous firing of the canine's sympathetic and vagal nerves. The solid line indicates the time the video in FIG. 3B was captured; dashed line is the time FIG. 3C was captured. Note that the dog was lying down during simultaneous sympathovagal discharge (FIG. 3A). Abrupt termination of the nerve discharges coincided with a change in posture from lying to sitting up (FIGS. 3B-3C). This was accompanied by an abrupt drop in the mean arterial pressure from 80 mmHg to 60 mmHg, a dramatic narrowing of the pulse pressure and an acceleration of HR. The video imaging in three dogs was collected and analyzed a total of 1000 episodes of abrupt simultaneous termination of sympathovagal discharges. Among these episodes, 390 were associated with sudden movement, such as standing up or starting to jump. In some episodes, it appeared that the dog was aroused (FIG. 3A). The second pattern of behavior is illustrated in FIGS. 3D-3E from a different dog. The dog was lying quietly on the floor and remained lying down during both the simultaneous sympathovagal discharges (solid line) and after the abrupt termination of the firing (dashed line). Note in FIG. 3D the mild drop in BP (from 110 mmHg to 100 mmHg, without narrowing of the pulse pressure) and tachycardia after the termination of sympathovagal discharges. These findings suggest that abrupt termination of sympathovagal discharge is the primary reason for transient hypotension and tachycardia. More dramatic changes in BP (hypotension associated with a narrow pulse pressure) occur when the dog terminated the sympathovagal discharge and concomitantly changed posture, possibly at the time of awakening (orthostatic hypotension).

Figure 4A:
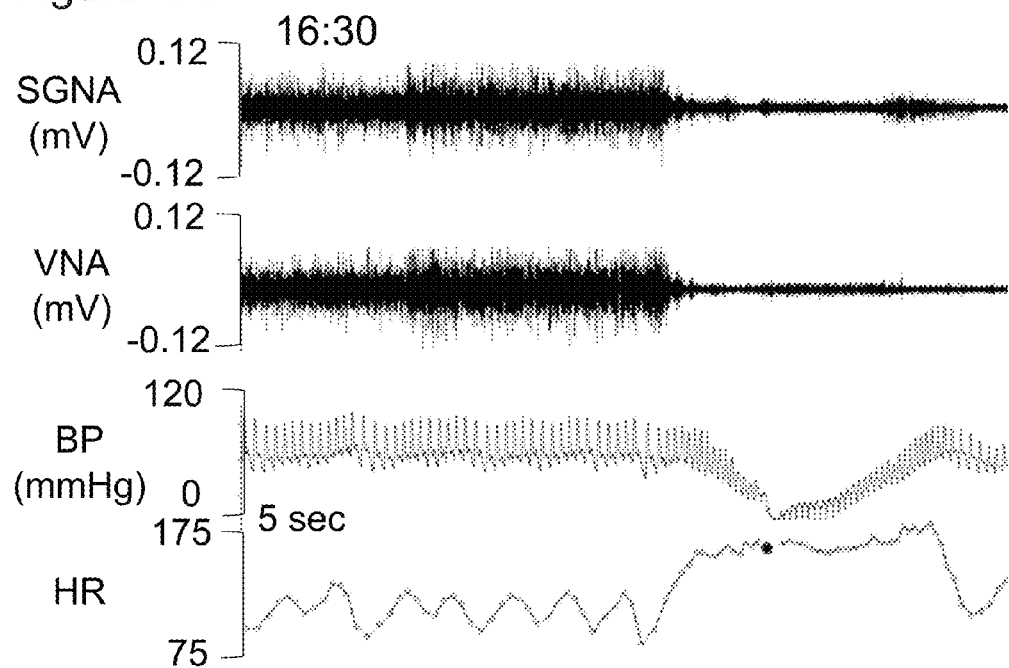
FIGS. 4A-4B depict circadian variation of the hypotensive (<70 mmHg) episodes as analyzed in the Examples.
Figure 4B:
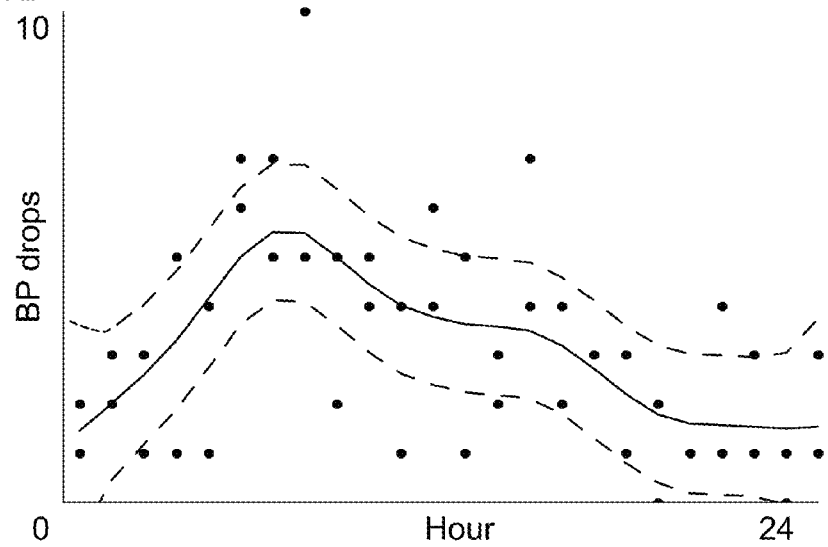

It is well-established that cardiac physiology has a circadian rhythm. In normal subjects, sympathetic tone is highest during the day and lowest at night when parasympathetic tone dominates. Likewise, arterial blood pressure is lowest overnight (about 10-20% lower than during the day) with peaks in pressure early in the morning after waking and again in late afternoon/early evening. Given the evidence in the above data that the offset of sympathovagal firing predicts hypotensive episodes, it is believed that the periods of hypotension may also have a circadian rhythm. FIGS. 4A and 4B show the circadian variation of the hypotensive episodes. FIG. 4A shows an example of extreme hypotension in the same dog as in FIGS. 1A-1D. The BP dipped to as low as 20 mmHg. The distribution of similar episodes (drop in pressure of 20 mmHg over 4 beats) throughout the day were manually analyzed and a significant ($p<0.0001$) circadian variation of the hypotensive episodes associated with sympathovagal termination was found (FIG. 4B).

Effects of Drugs on Nerve Activity and BP

The importance of sympathetic firing as it relates to large drops in blood pressure, led to a hypothesis that blocking sympathetic tone through a non-selective β-adrenoceptor antagonist such as carvedilol, or a specific β2-adrenoceptor antagonist, such as ICI, may decrease the frequency and severity of hypotensive episodes. The baseline BP was 125.60 (95% CI: 117.77 to 133.44) mmHg, which was insignificantly reduced by carvedilol to 124.8 (95% CI: 116.63 to 132.97) mmHg ($p=0.6788$), but was significantly increased to 133.00 (95% CI: 124.85 to 141.14) mmHg ($p=0.0001$) after 7 days of ICI infusion. The iSGNA immediately before drug was 209.40 (95% CI: 163.12 to 255.68) mV-s, which was significantly increased by carvedilol to 258.47 (95% CI: 207.20 to 309.75) mV-s ($p=0.0087$) and by ICI to 281.23 (95% CI: 230.30 to 332.16) mV-s ($p=0.0001$). The iVNA immediately before drug was 192.96 (95% CI: 130.58 to 254.62) mV-s, which was insignificantly decreased by carvedilol (186.68 mV-s, 95% CI: 122.83 to 250.53, $p=0.6433$), but was significantly increased by ICI to 220.18 (95% CI: 156.46 to 283.90) mV-s ($p=0.0293$). These findings indicate the ICI significantly increased SGNA, VNA and the BP. FIGS. 5A-5I shows examples of a canine at baseline (FIGS. 5A-5C), during carvedilol administration (FIGS. 5D-5F) and during ICI infusion (FIGS. 5G-5I), respectively. Note as in FIGS. 3A-3F, simultaneous sympathovagal withdrawal was followed by hypotension both at baseline and during carvedilol administration. However, simultaneous cessation of sympathovagal discharge during ICI infusion was not followed by hypotension.

Figure 6:
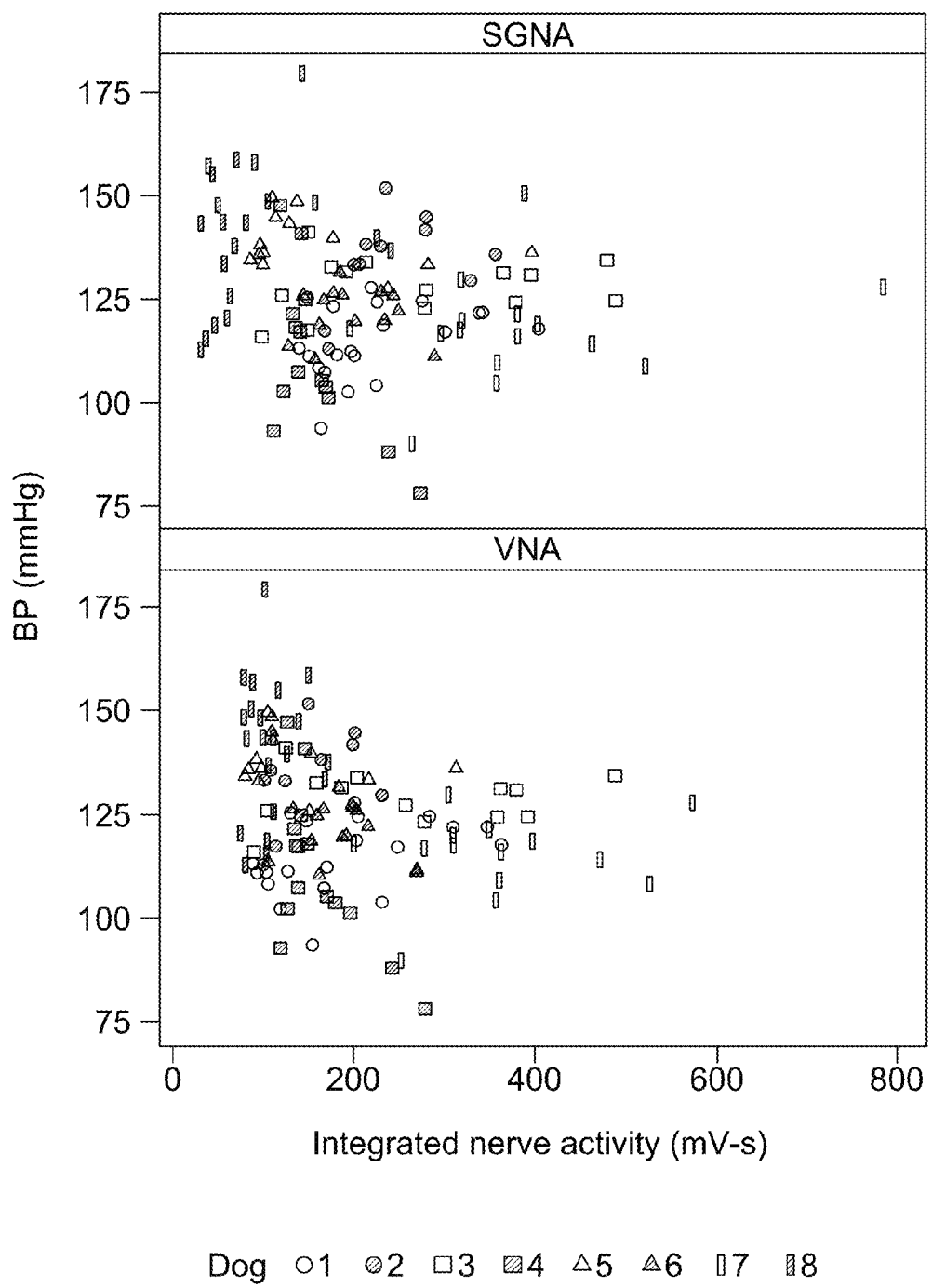
FIG. 6 depicts the relationship between nerve activity and BP at baseline in all dogs studied. Each dot represents a 4-hour integrated value. Note a large variation of SGNA, VNA and BP among different dogs. Although there is a significant relationship between integrated SGNA and BP ($p=0.0478$), the effect size was small. The integrated VNA was negatively correlated with the BP, but their relationship was statistically insignificant ($p=0.0648$).
Figure 7A:
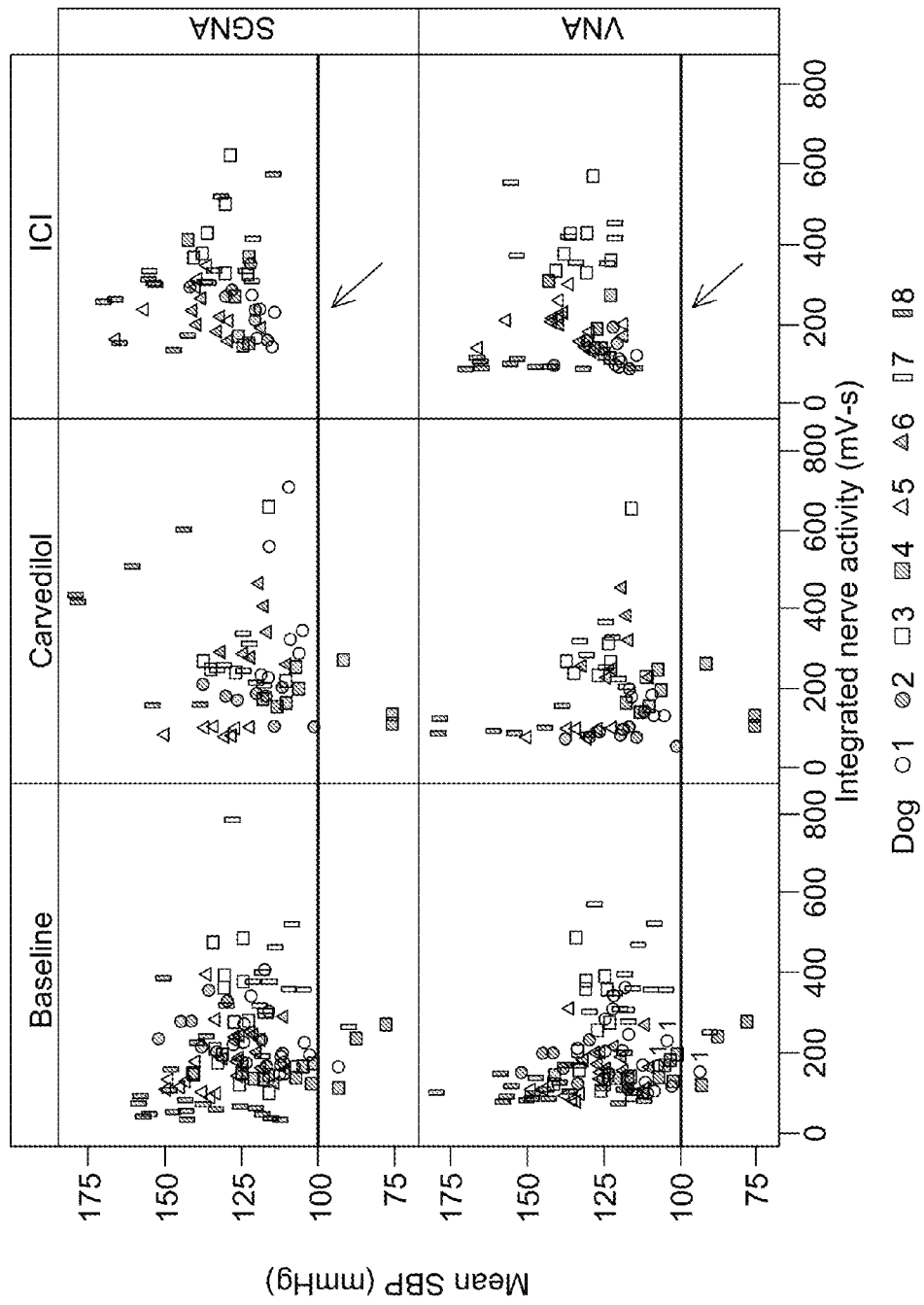
FIGS. 7A-7C depict effects of drugs on BP distribution as analyzed in the Examples.
Figure 7B:
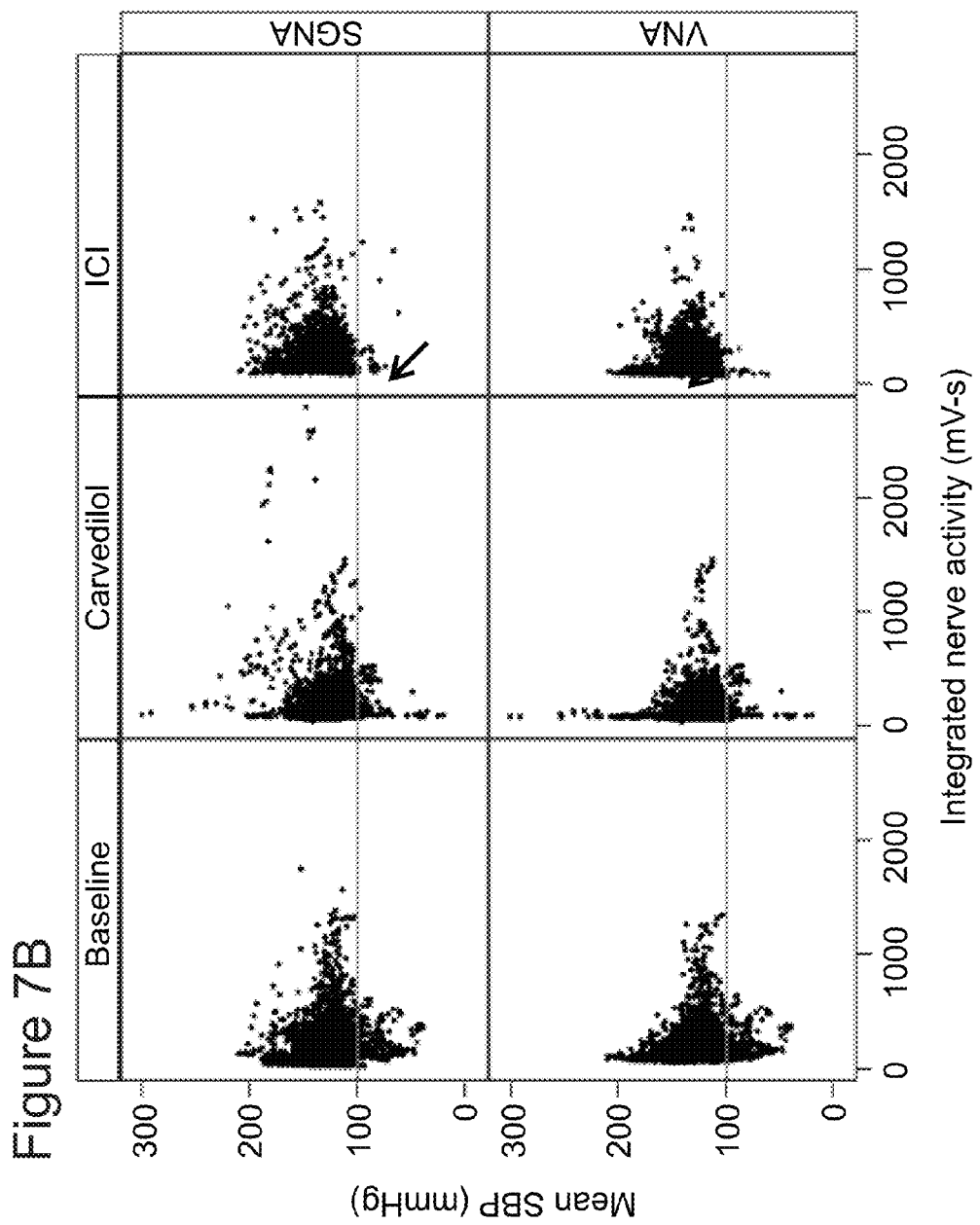
Figure 7C:
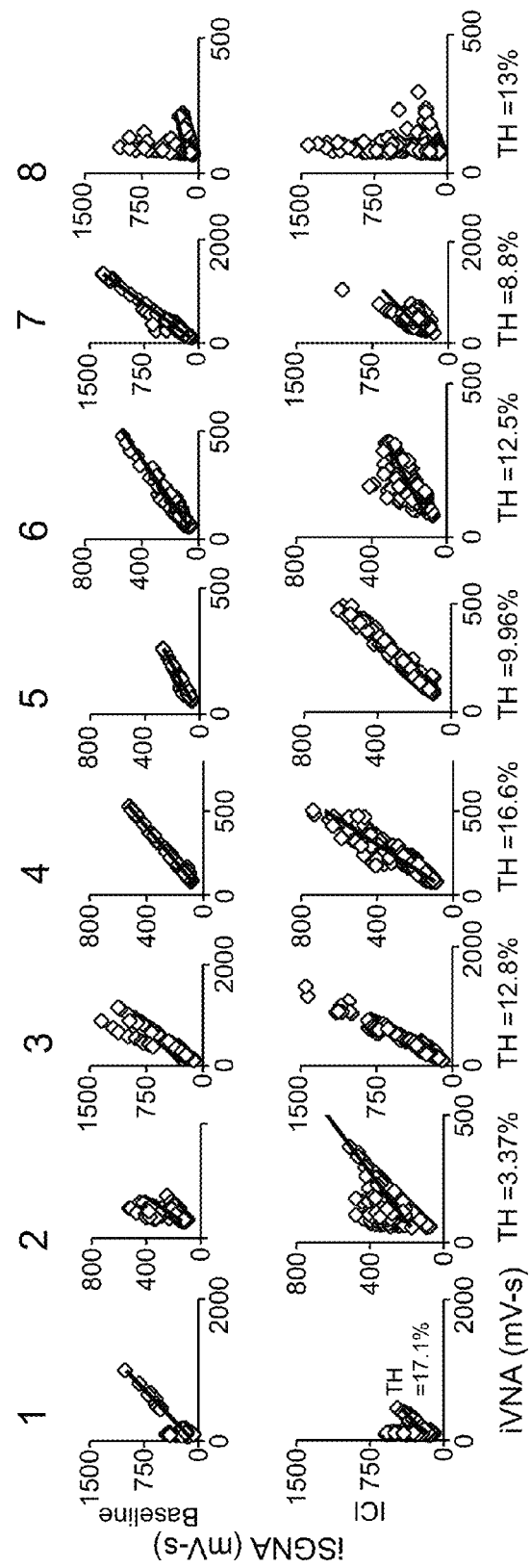
Figure 8A:
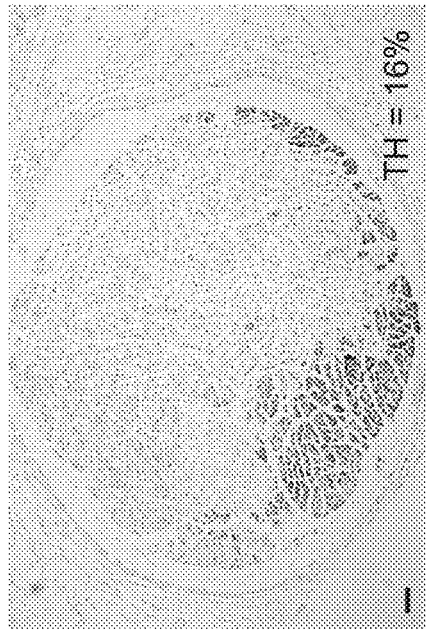
FIGS. 8A-8D depict tyrosine hydroxylase staining of the thoracic vagal nerves. Darker color identifies nerves that stained positively for tyrosine hydroxylase (TH).
Figure 8B:
Figure 8C:
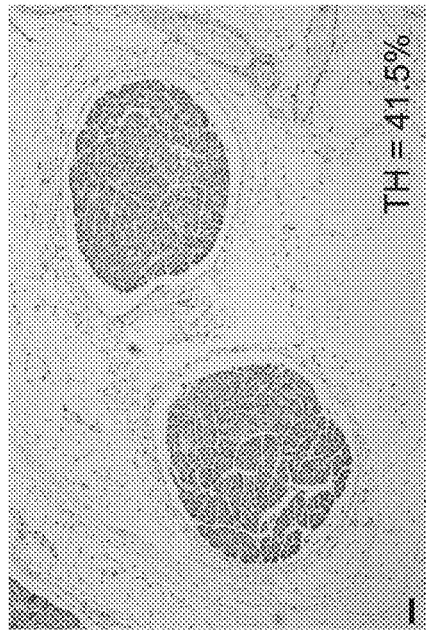
Figure 8D:
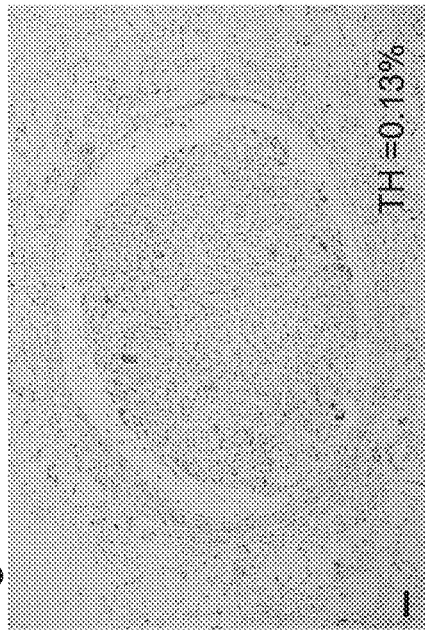

The relationship between SGNA, VNA and BP for all eight dogs at baseline is illustrated in FIG. 6. Each dot represents four hours of integrated nerve activity and the corresponding mean systolic blood pressure. Note that there is significant heterogeneity among dogs; this likely, in part, reflects the differences in group status. Dogs 1, 4 and 7 in the graph have the lowest mean SBP and were all Group 1 dogs; whereas the dogs with the highest SBP (5, 8) were Group 2. FIGS. 7A-7C illustrate the relationship between SGNA, VNA and BP during baseline, carvedilol and ICI infusion across all eight dogs. In FIG. 7A, each dot represents the average of 4 hours of integrated nerve activity; in FIG. 7B, each dot is one minute of integrated nerve activity. The line is drawn to mark 100 mmHg. Note the substantial increase in mean systolic BP between baseline and ICI recordings, but not between baseline and carvedilol in FIG. 7A. The mean BP (calculated over 4 hour intervals) during ICI infusion did not dip lower than 110 mmHg in any dog (arrows). In FIG. 7B, which represents the minute-by-minute data, the number of hypotensive episodes (defined as mean systolic pressure <100 mmHg in one min) were calculated for each dog. Each dot represents mean systolic BP over one minute. The percentage of hypotensive episodes during baseline was 7.1%; after carvedilol, 7.8% ($p=0.7475$) and after ICI, 1.3% ($p=0.0110$). These data show that ICI, but not carvedilol, significantly reduced hypotensive episodes. FIG. 7C shows the SGNA-VNA plots for each dog during baseline (row 1) and ICI infusion (row 2). Note the varied response to ICI infusion among all eight dogs. The absence of consistent response of the autonomic nervous system discharges suggests that ICI's effect on blood pressure occurs via modulation of the vascular β2-adrenoceptors and not through its effect on the cardiac autonomic nervous system.

Protocol 2: Thoracic Vagal Nerve Structure and Sympathovagal Correlation

The baseline nerve activity patterns were analyzed and the r values for sympathovagal correlation were determined in each of the 20 dogs. The SGNA-VNA correlation (r) averaged 0.61, SD=0.30 (range 4E-4 to 0.78). TH-positive components were present in the thoracic VN and accounted for an average of 14%, SD=10% (range 0.13% to 43.7%) of the cross sectional area (FIGS. 8A-8D: brown indicates areas of positive staining). There was only a weak positive correlation (Pearson correlation=0.17, $p<0.0001$) between r value and the percentage of TH-positive area staining. These findings, as well as that observed in FIGS. 2A-2D, suggest that the sympathovagal correlation, and hence the orthostasis, is determined both by the amount of TH-positive nerve structures in the vagal nerve and the physiological status of the dogs.

Discussion

Autonomic Nerve Activity and Postural Hypotension

The primary finding of this Example is that the simultaneous termination (offset) of SGNA and VNA may be associated with transient, but often dramatic, postural hypotension (>20 mmHg over 4 heart beats). Similar to that found in human subjects with postural hypotension syndrome (POTS), the offset hypotensive episodes in the dogs occurred more often in the morning than other times of the day. The mechanism of hypotension caused by cessation of simultaneous sympathovagal discharges is best explained by the following mechanisms: as shown in FIGS. 1A-1D, simultaneous sympathovagal discharges are associated with increased BP (sympathetic effect), but reduced HR (parasympathetic effect). Simultaneous termination of these two activities caused a sudden loss of sympathetic tone that reduced cardiac contraction and allowed peripheral vasodilatation. A sudden loss of parasympathetic tone allowed instantaneous heart rate acceleration, which transiently reduces ventricular filling and stroke volume. If simultaneous SGNA-VNA termination is followed by postural changes, then dramatic drops of BP and pulse pressure are observed.

There were significant similarities between the results of this Example and that found in human muscle sympathetic nerve activity (MSNA) studies during tilt table testing. Typically, upright tilt immediately increased MSNA. Further, an acute reduction of MSNA and BP was observed in patients with vasovagal syncope, but not in the controls. These findings are similar to those observed in Group 1 dogs, in which abrupt termination of SGNA was associated with an abrupt drop in BP. These results support the hypothesis that the final trigger for orthostatic hypotension is sympathetic nervous system inhibition.

In the above-described canine model, Group 2 dogs also had intermittent reduction of BP, although not as severe as in Group 1 dogs. Typically, elevated BP triggers a large increase of SGNA and a reduction of BP. Continuation of SGNA during BP reduction is similar to that found in some patients with vasovagal syncope.

Contribution of Vagal Nerve

In these Examples, VNA (or lack thereof) seems to be important in BP control. For example, simultaneous activation of VNA in Group 1 dogs may counterbalance the effects of SGNA and help maintain a relatively normal HR. These findings suggest that SGNA is the primary phenomenon whereas VNA is the secondary phenomenon that counterbalanced SGNA for BP and HR control. Abrupt termination of VNA allowed HR to increase, which leads to increased cardiac output and normalization of BP after transient orthostatic hypotension. Absence of VNA in Group 2 dogs implies that sympathetic tone alone controls the BP changes through vasoconstriction, vasodilation, and HR modulation. The differential patterns of VNA in these two groups of dogs suggest that more than one mechanism plays a role in the development of intermittent hypotensive episodes in dogs. The importance of VNA in hypotensive episodes in each dog is complicated by the fact that the grouping of dogs may change overtime. In addition, due to the complex physiology associated with vagal nerve activation, quantitative analyses using integrated vagal nerve activity may not be an optimal method for assessing vagal tone.

Beta 2 Receptor as a Potential Therapeutic Target for Postural Hypotension

It was further hypothesized that if hypotension occurs after the withdrawal of prolonged sympathovagal firing, then reducing the frequency and intensity of nerve firing may reduce the instances of hypotension. Studies in renal sympathetic nerves showed that stimulating prejunctional $\beta$2-adrenoceptors facilitates norepinephrine release. A previous clinical study showed that therapy with carvedilol caused significant decreases in systemic and cardiac norepinephrine spillover, an indirect measure of norepinephrine release. The authors of this previous study concluded that that carvedilol caused its sympatho-inhibitory effect by blocking peripheral, prejunctional $\beta$-adrenergic receptors. If the latter hypothesis is true, then carvedilol and ICI, both which block prejunctional $\beta$2-adrenoceptors, should reduce autonomic nerve activity and prevent orthostatic hypotension. This was not borne out in the instant Example; in fact, ICI led to an average increase in stellate and vagal nerve firing and carvedilol increased stellate firing though it had no impact on vagal firing. Furthermore, there is a large variation of nerve discharge responses to these drugs, suggesting large differences between dogs. While none of these drugs consistently reduce nerve firing, ICI did lead to an overall increase in BP by eliminating the hypotensive episodes. These findings are best explained by the effects of ICI on vascular $\beta$2 adrenoceptors. Previous work has shown that the $\beta$2 on blood vessels mediate vasodilation; therefore, blockade of these receptors through ICI (a $\beta$2 blocker) would be expected to cause vasoconstriction and thus increase BP. A previous study in a rat model of orthostatic hypotension showed that ICI had a tendency of improving orthostatic symptoms, but the authors did not show a definite beneficial effect. Although studies in humans have shown that ICI (in doses up to 80 mg orally) does not alter BP or heart rate, that study did not perform continuous BP monitoring. The postural hypotensive episodes may not have been detected in that study. The results of the instant Example suggest that in the canine model, ICI may be an effective therapy for orthostatic hypotension.

Anatomical Basis of SGNA-VNA Coordination

A study to quantitate the amount of TH-positive (catecholamine producing) nerve structures within the cervical and thoracic vagal nerve was conducted. The results showed a large variation of sympathetic nerve content among dogs. These findings suggest that if a greater sympathetic component is present in the vagal nerve, then it is more likely that the VNA will occur simultaneously with SGNA. Therefore, the thoracic vagal nerves of dogs from the present Example were studied, as well as those from previous studies, to determine the quantity of sympathetic component in the thoracic vagal nerve. Only a very weak, although significant, correlation between sympathetic nerve staining in the vagal nerve and SGNA-VNA coordination was found. Furthermore, there is evidence of changing coordination patterns over a 5-month period in dogs with prolonged monitoring. These findings suggest a combined anatomical and physiological mechanism for SGNA-VNA coordination.

CONCLUSIONS

Coordination between SGNA and VNA is important in determining the BP of ambulatory dogs. Simultaneous SGNA-VNA activation and withdrawal play an important role in postural hypotension. The SGNA-VNA correlation is only partially determined by the amount of sympathetic nerve structures in the thoracic vagus.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for treating orthostatic hypotension in a subject in need thereof, the method comprising administering a therapeutically effective amount of a $\beta$2-adrenoceptor antagonist to the subject, wherein the $\beta$2-adrenoceptor antagonist is 3 (isopropylamino)-1-[(7-methyl-4-indanyl)oxy]butan-2-ol.

2. The method of claim 1 wherein the subject is administered from about 1 µg/kg/hr to about 5 µg/kg/hr of the $\beta$2-adrenoceptor antagonist for a period of about 7 days.

3. The method of claim 1 wherein about 10 mg to about 40 mg of the β2-adrenoceptor antagonist is orally administered to the subject.

4. The method of claim 1 wherein the subject is an elderly subject.

5. A method for treating dizziness resulting from orthostatic hypotension in a subject in need thereof, the method comprising administering a therapeutically effective amount of a β2-adrenoceptor antagonist to the subject, wherein the β2-adrenoceptor antagonist is 3 (isopropylamino)-1-[(7-methyl-4-indanyl)oxy]butan-2-ol.

6. The method of claim 5 wherein about 1 μg/kg/hr to about 5 μg/kg/hr of the β2-adrenoceptor antagonist is administered to the subject for a period of about 7 days.

7. The method of claim 5 about 10 mg to about 40 mg of the β2-adrenoceptor antagonist is orally administered to the subject.

* * * * *